United States Patent [19]
Yamaguchi

[11] Patent Number: 6,121,013
[45] Date of Patent: Sep. 19, 2000

[54] METHOD FOR CROSS-LINKING PROTEIN BY USING ENZYME

[75] Inventor: Shotaro Yamaguchi, Norwich, United Kingdom

[73] Assignee: Amano Pharmaceutical Co., Ltd., Aichi, Japan

[21] Appl. No.: 09/280,859

[22] Filed: Mar. 30, 1999

[30] Foreign Application Priority Data

Mar. 31, 1998 [JP] Japan .................................. 10-105729

[51] Int. Cl.⁷ .............................. C12P 21/06; C12N 9/02
[52] U.S. Cl. ......................... 435/68.1; 435/189; 530/402
[58] Field of Search .................................. 435/68.1, 189; 530/402

[56] References Cited

U.S. PATENT DOCUMENTS 5,899,212  5/1999  Sorensen et al. ....................... 132/203

OTHER PUBLICATIONS

Cooper et al., Biochem. Biophys. Res. Commun., 112(1): 161–167, Apr. 15, 1983.
Faergemand et al., J. Agric. Food Chem., 46(4): 1326–1333, Mar. 18, 1998.
Communication from European Patent Office, Feb. 15, 2000 enclosing European Search Report with Annex (3 pages).
Faergemand M et al: "Cross–linking of whey proteins by enzymatic oxidation" Journal of Agricultural Food Chemistry, vol. 46, No. 4, Mar. 18,1998 (1998–03–18), pp. 1326–1333, XO000867797 p. 1327, paragraph 1–3, p. 1329, paragraph 4–p. 1330, paragraph 2; figures 5,6; table 1 p.1332, paragraph 2,3.
Matheis, G and WhitakerJ.R.: "A review: Enzymatic cross–linking of proteins applicable to food" Journal of Food Biochemistry, vol. 11, No. 4, 1987, pp. 309–327, XP00087468, Connecticut, USA pp. 309–320.
Figueroa–Espinoza M C et al: "Oxidative Cross–Linking of Pentosans by a Fungal Laccase and Horseradish Peroxidase: Mechanism of Linkage between Feruloylated Arabinoxylans" Cereal Chemistry, US, American Association of Cereal Chemists. Minneapolis, vol. 75, No. 2, Mar. 1, 1998 (1998–03–01), pp. 259–265, XP000739677, ISSN: 0009–0352, p. 259–p. 260, p. 263; figure 2.

*Primary Examiner*—Francisco Prats
*Assistant Examiner*—Susan D. Coe
*Attorney, Agent, or Firm*—Sughrue, Mion, Zinn, Macpeak & Seas, PLLC

[57] ABSTRACT

A novel method for cross-linking a protein, which uses a multi-copper oxidase such as laccase, bilirubin oxidase, and the like.

18 Claims, 5 Drawing Sheets

1  2  3  4  5  6  7  8  9  10  11  12

1 2 3 4 5 6 7 8

1 2 3 4 5 6 7 8 9 10 11 12

1  2  3  4  5  6  7  8

METHOD FOR CROSS-LINKING PROTEIN BY USING ENZYME

FIELD OF THE INVENTION

This invention relates to a novel method for cross-linking a protein using an enzyme. More particularly, it relates to a novel method for cross-linking protein using a multi-copper oxidase such as laccase or bilirubin oxidase.

BACKGROUND OF THE INVENTION

Protein materials which are cross-linked to have a high molecular weight or gelled by the cross-linking method of the present invention can be used in the field of food processing such as of raw fish meat paste, kamaboko (fish cake), fish/livestock meat sausage, tofu (soy bean curd), noodles, confectionery/bread, food adhesives, sheet-like meat food, yogurt, jelly and cheese. In addition, they can also be used as novel protein-derived materials in a wide range of industries including cosmetics, raw materials of microcapsules and carriers of immobilized enzymes.

As enzymes having a possibility of increasing molecular weight of protein by cross-linking reaction, transglutaminase, lysyl oxidase, protein disulfide-isomerase, protein-disulfide reductase, sulfhydryl oxidase, lipoxygenase, polyphenol oxidase (tyrosinase) and peroxidase have been known (Matheis and Whitaker, J. Food Biochemistry, 11, 309–327, 1987).

Among the above-described enzymes having a possibility of increasing molecular weight of protein by cross-linking reaction, a method for cross-linking protein by transglutaminase is well known. It is also known that this method has been broadly used mainly in the field of food processing based on the discovery of an inexpensive microbial transglutaminase which does not require the presence of calcium for the reaction (JP-B-6-65280 (the term "JP-B" as used herein means an "examined Japanese patent publication"), Agric. Biol. Chem., vol. 69, no. 10, pp. 1301–1308).

The protein cross-linking reaction by transglutaminase, however, has the following problem. That is, since transglutaminase is an enzyme which forms an intramolecular or intermolecular bridge structure of protein as a result of the acyl rearrangement reaction generated between the γ-carboxyl group of glutamine residue and the ε-amino group of lysine residue in a protein, some species of protein can hardly become the substrate for the enzyme due to insufficient glutamine residues or lysine residues. For example, albumin proteins cannot be used as the substrate for transglutaminase under their native state.

Thus, although a possibility of using several enzymes as the enzyme-aided protein cross-linking method has been indicated, most of them are not sufficiently useful in their supplying amounts, costs, easiness in the purification, and the like. Even if the microbial transglutaminase is used for the cross-linking method, its application is limited because of a problem that the reaction does not occur in some protein species. In consequence, great concern has been directed toward the development of a protein cross-linking method which uses other enzymes.

SUMMARY OF THE INVENTION

The inventor of the present invention has conducted extensive studies on the the possiblity of cross-linking reaction of protein using a multi-copper oxidase such as laccase, bilirubin oxidase, ascorbic acid oxidase and ceruloplasmin and, as a result, found that protein can be cross-linked by the use of these enzymes. Based on the finding of the novel method for cross-linking protein using a multi-copper oxidase such as laccase, bilirubin oxidase, ascorbic acid oxidase or ceruloplasmin, the present invention provides a protein cross-linking method which has a completely different reaction mechanism from that of transglutaminase and which can produce gelled protein having new physical properties and characteristics, with expanding the range of protein species to be treated which were limited in the known protein cross-linking method by transglutaminase.

The present inventors have made screening of a broad range of natural resources for finding a novel enzyme which can increase molecular weight of protein and makes it to gel by a cross-linking reaction and, as a result, found that certain enzymes classified as multi-copper oxidase can increase molecular weight of protein to make it gel by directly acting upon the protein, thus resulting in the accomplishment of the present invention.

DETAILED DESCRIPTION OF THE INVENTION

Figure 1:
FIG. 1 is a figure showing migration pattern of SDS-polyacrylamide gel electrophoresis in Example 1.

The term "multi-copper oxidase" as used herein means a group of enzymes which have a plurality of copper atoms in one molecule and oxidize polyphenol, methoxyphenol, diamine, bilirubin or ascorbic acid by molecular oxygen. The number of copper atoms so far known is generally from 2 to 8, but the number of copper atoms is not particularly limited because the number varies depending on the condition of enzyme preparations to be analyzed and the analyzing method. Examples of enzymes classified as the multi-copper oxidase include laccase, bilirubin oxidase, ascorbic acid oxidase and ceruloplasmin. Laccase and bilirubin are particularly preferable.

Laccase ([EC 1.10.3.2]) is a multi-copper protein enzyme having low substrate specificity acting upon o-quinol and p-quinol or sometimes upon aminophenol and phenylenediamine as well. The semiquinone formed further undergoes an enzymatic or non-enzymatic reaction. Examples of laccase include those which are originated from plants such as lacquer and microorganisms such as bacteria and fungi, and examples of the microbial laccase include those enzymes produced by the genera Aspergillus, Neurospora, Podospora, Botrytis, Collybia, Fomes, Lentinus, Pleurotus, Pycnoporous, Pyricularia, Trametes, Rhizoctonia, Rigidoporus, Coprinus, Psatyrella, Myceliophtera, Schtalidium, Polyporus, Phlebia and Coriolus.

Bilirubin oxidase (EC 1.3.3.5) is a multi-copper protein enzyme which acts mainly upon bilirubin, and examples of such bilirubin oxidase include those enzymes produced by the genera Penicillium, Myrothecium and Trachyderma.

Ascorbic acid oxidase (EC 1.10.3.3) is a multi-copper protein enzyme which acts mainly upon L-ascorbic acid and is originated from plants such as cucumber, pumpkin and zucchini and microorganisms such as bacteria and fungi.

Ceruloplasmin (EC 1.16.3.1) is a multifunctional protein belonging to the multi-copper protein, which maintains homeostasis of copper in the living body, has ferroxidase activity and amine oxidase activity and is present in sera of animals and birds.

In this connection, tyrosinase (catecholase, EC 1.10.3.1) and phenolase (cresolase, EC 1.14.18.1) are known as enzymes which carry out similar reactions to those of the multi-copper oxidase, and they are also copper-containing enzymes, but the former is an enzyme that acts upon catechols and the latter shows the same reaction of the former only when 1,2-benzenediol is present, so that these enzymes are different from the group of multi-copper oxidase. This is also evident from the recently developed grouping method based on the homology of amino acid sequences and three-dimensional structures obtained by X-ray analysis.

That is, cysteine, histidine or methionine (not essential) has been identified as the ligand amino acid of copper atom in the enzymes of the multi-copper oxidase group (A. Messerschmidt and R. Huber, *Eur. J. Biochem.*, 187, 341–352, 1990), but histidine is the only ligand amino acid of the enzymes of the tyrosinase group (K. Lerch, *ACS Symposium Series*, 600, 64–80, 1995). Also, amino acid sequences around the ligand amino acid have certain homology within each group, but the homology is obviously low between the two groups.

The method for gelling protein using multi-copper oxidase is further described. As described in the foregoing, the multi-copper oxidase used in the present invention may be obtained from any one of supply sources such as animals, plants and microorganisms. It may also be a microbial product accumulated as an intracellular or extracellular enzyme. In addition, it may be not only a naturally occurring enzyme but also an enzyme produced by means of genetic engineering techniques or cell engineering techniques or an enzyme protein modified by protein engineering techniques. Though it is desirable to use a purified high purity multi-copper oxidase in the present invention, the degree of its purity is not limited with the proviso that desired reactions can be effected. Also, these enzyme preparations may contain various salts, saccharides, proteins, lipids and surface active agents as stabilizers of the enzyme.

The substrate protein to be used in the present invention may be of any species and is not restricted by its origin and properties, with the proviso that it receives actions of the aforementioned enzymes. Its examples include plant proteins derived from beans and cereals and animal proteins including milk proteins such as casein and β-lactoglobulin, egg proteins such as ovalbumin, meat proteins such as myosin and actin, blood proteins such as serum albumin and tendon proteins such as gelatin and collagen. It may also be a protein partially hydrolyzed chemically with an acid or alkali or enzymatically with a protease, a protein chemically modified with various reagents or a synthesized peptide.

These substrate proteins are subjected to the reaction in the form of a solution, slurry or paste, but the concentration of each form is not particularly limited and it is optionally selected depending on the desired properties and conditions of the cross-linked protein of interest. In general, a solution with increased viscosity or a precipitate is obtained when the concentration is low, or a gelled product when the concentration is high, and a gelled product can be obtained satisfactorily when the concentration is 1% by weight or more.

In addition, such a solution, slurry or paste of the substrate protein may be obtained not only in an aqueous form but also as an emulsion with an oil or fat and, as occasion demands, may be blended with additives such as salts, saccharides, proteins, perfumes, moisture keeping agents and coloring agents.

Amount of the enzyme to be used, time and temperature of the reaction and pH of the reaction solution are not particularly limited, but a cross-linked or gelled protein having increased molecular weight can generally be obtained when the reaction is carried out for a period of from 10 seconds to 48 hours, preferably from 10 minutes to 24 hours, using the enzyme in an amount of from 0.5 to $1 \times 10^6$ units, preferably from 5 to $1 \times 10^5$ units, per 1 g of protein, at a reaction temperature of from 5 to 80° C., preferably from 20 to 60° C., and at a reaction solution pH of from 2 to 10, preferably from 4 to 8. These reaction conditions are optionally selected depending on physical properties and moisture content of the intended cross-linked or gelled protein.

Also, various polyphenols such as hydroquinone, catechol, guaiacol, ferulic acid, vanillic acid, p-coumaric acid, syring aldehyde and p-phenylenediamine may be added as a mediator which accelerates the reaction of multi-copper oxidase.

Mechanism of the molecular weight-increasing cross-linking reaction of protein by multi-copper oxidase in the present invention is considered as follows. In general, the reaction of oxidase is a reaction in which protons are removed from a substrate to be oxidized in the presence of molecular oxygen, thereby forming oxidized substrate and water. Amino acid side chains of protein as the substrate to be used in the present invention contain certain functional groups which are apt to be oxidized, such as hydroxyl group of tyrosine, sulfhydryl group of cysteine, ε-amino group of lysine and imidazole group of histidine. On the other hand, laccase as a typical multi-copper oxidase is well known as an enzyme which has broad substrate specificity.

In consequence, functional groups with increased reactivity are formed when these enzymes act upon the aforementioned side chain functional groups. For example, the side chain of tyrosine becomes o-quinone which is rich in reactivity and reacts mutually with quinone or with other amino group or sulfhydryl group. It is well known that sulfhydryl groups together form an S—S cross-link when oxidized. It is well known also that ε-amino group of lysine forms aldehyde having high reactivity by receiving oxidative deamidation and thereby forms a Schiff base with other amino group. When these reactions occur between different proteins, a reaction product whose molecular weight is increased by cross-linking is formed.

The following illustrates the present invention with reference to examples. In this connection, measurement of the enzyme activity of laccase was carried out by the following method using 2,2'-azino-di-[3-ethylbenzthiazoline sulfonate (6)] (ABTS, manufactured by Boehringer-Mannheim) as the substrate unless otherwise noted.

Activity Measuring Method

ABTS is dissolved in 25 mM citrate buffer (pH 3.2) to a concentration of 1.0 mg/ml and used as the substrate solution. A 3.0 ml portion of this substrate solution is put into a cuvette, pre-incubated at 25° C. and then mixed with 0.1 ml of enzyme solution, and the mixture is stirred and incubated at 25° C. to measure absorbance at 405 nm after 1 minute and 3 minutes. The amount of enzyme which increases the absorbance at 405 nm by a factor of 1.0 OD within 1 minute under these conditions was defined as 1 unit.

EXAMPLE 1
Cross-linking of Protein by *Pycnoporus coccineus* Laccase

As the substrate proteins, (1) milk casein (Hammarsten, manufactured by Merck), (2) bovine serum albumin (manufactured by Armour Pharma) and (3) gelatin (manufactured by Wako Pure Chemical Industries) were used. Using a reaction solution containing 5% by weight (final concentration) of each of these proteins, 50 mM (final concentration) of potassium-sodium phosphate buffer (pH 7.0) and 2 units per 1 mg substrate protein of *Pycnoporus coccineus* laccase (product name: Laccase P, manufactured by Funakoshi), the reaction was carried out by stirring the reaction solution and then allowing it to stand at 37° C. for 17 hours. After completion of the reaction, a portion of the reaction solution was sampled and subjected to SDS-polyacrylamide gel electrophoresis using 2 to 25% polyacrylamide gel to observe increase in the molecular weight of substrate protein, thereby judging results of the cross-linking.

As a control test, the same reaction was carried out by replacing the enzyme with Streptoverticillium transglutaminase (prepared in accordance with the method described in Agric. *Biol. Chem.*, vol. 53, no. 10, pp. 2613–2617, 1989) or horseradish peroxidase (manufactured by Tokyo Kasei). The *Streptoverticillium transglutaminase* was added in an amount of 0.002 unit per 1 mg substrate protein, and, in the case of the horseradish peroxidase, it was added in an amount of 4 µg per 1 mg substrate protein, together with 4 µg per 1 mg substrate protein of Aspergillus niger glucose oxidase (product name: Glucose Oxidase "Amano" I, manufactured by Amano Pharmaceutical Co., Ltd.) and 10 mM in final concentration of glucose. The results are shown in FIG. 1, and conditions of each lane in FIG. 1 are shown in the following Table 1.

TABLE 1

| Lane | Substrate protein | Enzyme |
| --- | --- | --- |
| 1 | Casein | No addition |
| 2 | Casein | Transglutaminase |
| 3 | Casein | *Pycnoporus coccineus laccase* |
| 4 | Casein | *Horseradish peroxidase* |
| 5 | BSA * | No addition |
| 6 | BSA | Transglutaminase |
| 7 | BSA | *Pycnoporus coccineus laccase* |
| 8 | BSA | *Horseradish peroxidase* |
| 9 | Gelatin | No addition |
| 10 | Gelatin | Transglutaminase |
| 11 | Gelatin | *Pycnoporus coccineus laccase* |
| 12 | Gelatin | *Horseradish peroxidase* |

*: Bovine serum albumin

As shown in FIG. 1, molecular weight of each of the substrate proteins was increased through the cross-linking case. On the contrary, the generally known *Streptoverticillium transglutaminase* and horseradish preoxidase showed the effect to increase molecular weights of milk casein and gelatin by the cross-linking reaction, but they do not exert such an effect upon bovine serum albumin.

EXAMPLE 2
Preparation of *Coriolus versicolor* Laccase

*Coriolus versicolor* (IFO 08753) was inoculated into 200 ml of a medium (pH 5.0) composed of 3.0% glucose, 1.0% peptone, 0.14% potassium dihydrogen phosphate, 0.05% magnesium sulfate heptahydrate, 0.002% thiamin hydrochloride and 0.002% copper sulfate pentahydrate and cultured on a shaker at 28° C. for 11 days, the thus obtained seed culture broth was inoculated into 25 liters of a medium (pH 5.0) composed of 3.0% glucose, 1.0% peptone, 0.14% potassium dihydrogen phosphate, 0.05% magnesium sulfate heptahydrate, 0.002% thiamin hydrochloride, 0.002% copper sulfate pentahydrate and 0.01% Adecanol LG126 (trade name, manufactured by Asahi Denka Kogyo) as an anti-foaming agent and cultured with aeration and agitation at 28° C. for 10 days, and then the resulting cells were removed by filtration to obtain 20 liters of culture filtrate.

The culture filtrate was concentrated to 4 liters using an ultrafiltration membrane AIP 1010 (trade name, manufactured by Asahi Chemical Industry) and then dialyzed against 10 mM phosphate buffer (pH 6.0). The thus dialyzed solution was applied to a column packed with DEAE-Sepharose CL-6B (trade name, manufactured by Pharmacia) which has been equilibrated in advance with the same buffer, and the elution was carried out using the same buffer with a sodium chloride density gradient of from 0 to 0.5 M to obtain laccase-active fractions to be used as the enzyme solution. The activity of this enzyme solution was found to be 1988.1 units/ml.

EXAMPLE 3
Cross-linking of protein by *Coriolus versicolor* Laccase

As the substrate proteins, milk casein (Hammarsten, manufactured by Merck) and gelatin (manufactured by Wako Pure Chemical Industries) were used. Using a reaction solution containing 1, 3 or 5% by weight (final concentration) of each of these proteins, 50 mM (final concentration) of potassium-sodium phosphate buffer (pH 7.0) and 2 units per 1 mg substrate protein of *Coriolus versicolor* laccase prepared in Example 2, the reaction was carried out by stirring the reaction solution and then allowing it to stand at 37° C. for 17 hours. After completion of the reaction, a portion of the reaction solution was sampled and subjected to SDS-polyacrylamide gel electrophoresis using 2 to 25% polyacrylamide gel to observe increase in the molecular weight of substrate protein, thereby judging results of the cross-linking. The results are shown in FIG. 2, and conditions of each lane in FIG. 2 are shown in the following Table 2.

TABLE 2

| Lane | Substrate protein (conc.) | Enzyme |
| --- | --- | --- |
| 1 | Casein (5 w/w %) | *Coriolus versicolor laccase* |
| 2 | Casein (3 w/w %) | *Coriolus versicolor laccase* |
| 3 | Casein (1 w/w %) | *Coriolus versicolor laccase* |
| 4 | Casein (3 w/w %) | No addition |
| 5 | Gelatin (5 w/w %) | *Coriolus versicolor laccase* |
| 6 | Gelatin (3 w/w %) | *Coriolus versicolor laccase* |
| 7 | Gelatin (1 w/w %) | *Coriolus versicolor laccase* |
| 8 | Gelatin (3 w/w %) | No addition |

Figure 2:
FIG. 2 is a figure showing migration pattern of SDS-polyacrylamide gel electrophoresis in Example 3.

As shown in FIG. 2, molecular weight of each substrate protein was increased by cross-linking at each concentration. The degree of molecular weight increase by cross-linking and viscosity of the reaction product became high as the protein concentration increased, so that the product from the 1% by weight protein did not flow out from its container when it was turned upside down, and a gelled product having strong elasticity was formed from the 5% by weight protein.

EXAMPLE 4

Cross-linking of Protein by *Myrothecium verrucaria* Bilirubin Oxidase

As the substrate proteins, (1) milk casein (Hammarsten, manufactured by Merck), (2) gelatin (manufactured by Wako Pure Chemical Industries) and (3) bovine serum albumin (manufactured by Armour Pharma) were used. Using a reaction solution containing 5% by weight (final concentration) of each of these proteins, 50 mM (final concentration) of potassium-sodium phosphate buffer (pH 7.0) and *Myrothecium verruvcaria* bilirubin oxidase (BO-3, manufactured by Amano Pharmaceutical Co., Ltd.) and its recombinant bilirubin oxidase, the reaction was carried out by stirring the reaction solution and then allowing it to stand at 37° C. for 17 hours. After completion of the reaction, a portion of the reaction solution was sampled and subjected to SDS-polyacrylamide gel electrophoresis using 2 to 25% polyacrylamide gel to observe increase in the molecular weight of substrate protein, thereby judging results of the cross-linking. The *Myrothecium verruvcaria* bilirubin oxidase was added in an amount of 2.9 units per 1 mg substrate protein, and two types of recombinant bilirubin oxidase obtained using *Aspergillus oryzae* and *Penicillium camembertii* as respective hosts were used and added in an amount of 3.0 units for the former, and 3.6 units for the latter, per 1 mg of the substrate protein.

Figure 3:
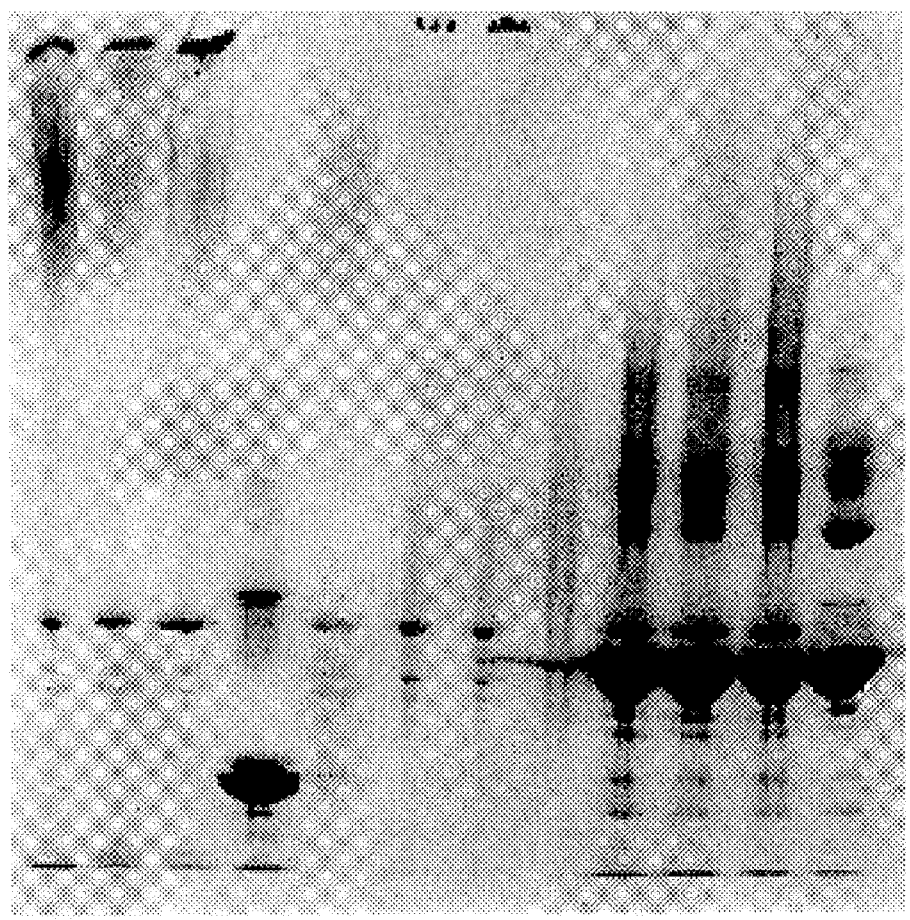
FIG. 3 is a figure showing migration pattern of SDS-polyacrylamide gel electrophoresis in Example 4.

The recombinant bilirubin oxidase was prepared by obtaining a transformant strain in accordance with the method described in JP-A-6-245777 (the term "JP-A" as used herein means an "unexamined published Japanese patent application"), culturing the strain, concentrating the thus obtained culture filtrate using an ultrafiltration membrane AIP 1010 (trade name, manufactured by Asahi Chemical Industry) and then dialyzing it against 10 mM phosphate buffer (pH 6.0). The thus dialyzed solution was applied to a column packed with DEAE-Sepharose CL-6B (trade name, manufactured by Pharmacia) which has been equilibrated in advance with the same buffer, and the elution was carried out using the same buffer with a sodium chloride density gradient of from 0 to 0.5 M to obtain a bilirubin oxidase-active fraction. This fraction was concentrated using a centrifugation type ultrafiltration membrane MacroSep 3K (trade name, manufactured by Pal Filtron), applied to a column packed with Sephacryl S-200 (trade name, manufactured by Pharmacia) which has been equilibrated in advance with the same buffer, and then the elution was carried out using the same buffer to obtain a bilirubin oxidase-active fraction. This fraction was concentrated using the centrifugation type ultrafiltration membrane MacroSep 3K and used as the enzyme solution. The results are shown in FIG. 3, and conditions of each lane in FIG. 3 are shown in Table 3.

TABLE 3

| Lane | Substrate protein | Enzyme |
| --- | --- | --- |
| 1 | Casein | *Myrothecium bilirubin oxidase* |
| 2 | Casein | *Penicillium recombinant bilirubin oxidase* |
| 3 | Casein | *Aspergillus recombinant bilirubin oxidase* |
| 4 | Casein | No addition |
| 5 | Gelatin | *Myrothecium bilirubin oxidase* |
| 6 | Gelatin | *Penicillium recombinant bilirubin oxidase* |
| 7 | Gelatin | *Aspergillus recombinant bilirubin oxidase* |
| 8 | Gelatin | No addition |
| 9 | BSA * | *Myrothecium bilirubin oxidase* |
| 10 | BSA | *Penicillium recombinant bilirubin oxidase* |
| 11 | BSA | *Aspergillus recombinant bilirubin oxidase* |
| 12 | BSA | No addition |

*: Bovine serum albumin

As shown in FIG. 3, the cross-linked increase of molecular weight of each substrate protein was effected by all of the bilirubin oxidase preparations.

EXAMPLE 5

Cross-linking of Protein by *Rigidoporus zonalis* Laccase and *Trachyderma tunodae* Bilirubin Oxidase As the substrate proteins, (1) milk casein (Hammarsten, manufactured by Merck) and (2) bovine serum albummin (manufactured by Armour Pharma) were used. Using a reaction solution containing 5% by weight (final concentration) of each of these proteins, 50 mM (final concentration) of potassium-sodium phosphate buffer (pH 7.0) and *Rigidoporus zonalis* laccase (manufactured by Takara Shuzo) or *Trachyderma tunodae* bilirubin oxidase (manufactured by Takara Shuzo), the reaction was carried out by stirring the reaction solution and then allowing it to stand at 37° C. for 17 hours. After completion of the reaction, a portion of the reaction solution was sampled and subjected to SDS-polyacrylamide gel electrophoresis using 2 to 25% polyacrylamide gel to observe increase in the molecular weight of substrate protein, thereby judging results of the cross-linking.

Figure 4:
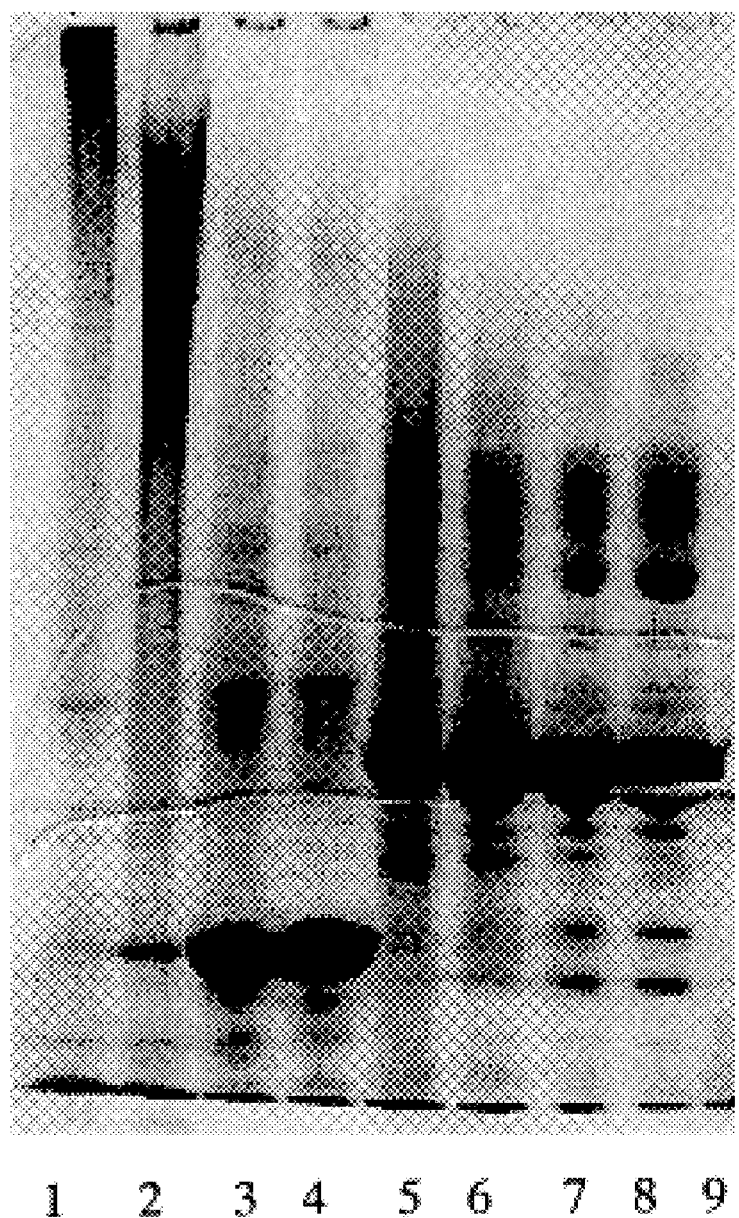
FIG. 4 is a figure showing migration pattern of SDS-polyacrylamide gel electrophoresis in Example 5 when *Rigidoporus zonalis* laccase was used.
Figure 5:
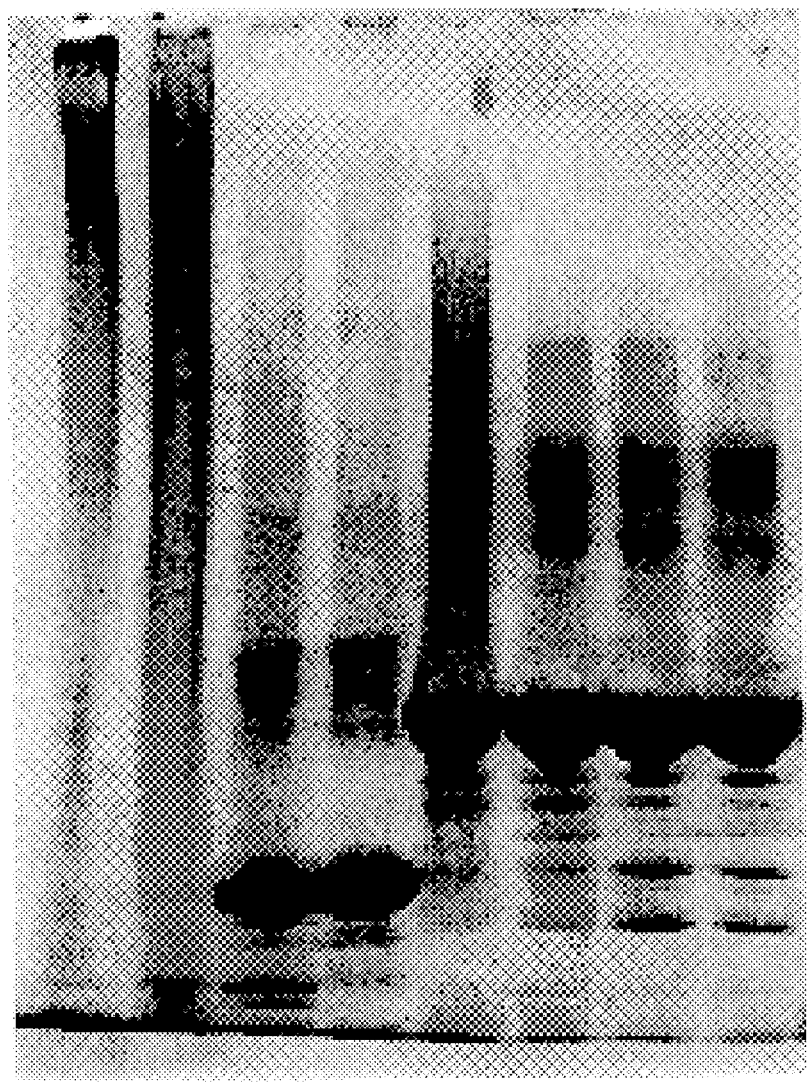
FIG. 5 is a figure showing migration pattern of SDS-polyacrylamide gel electrophoresis in Example 5 when *Trachyderma tunodae* bilirubin oxidase was used.

The amount of enzymes used was 2.22 units, 0.222 unit or 0.022 unit per 1 mg of the substrate protein in the case of *Rigidoporus zonalis* laccase and 5.58 units, 0.558 unit or 0.056 unit per 1 mg of the substrate protein in the case of *Trachyderma tunodae* bilirubin oxidase The results are shown in FIGS. 4 and 5, and conditions of each lane in FIGS. 4 and 5 are shown in Tables 4 and 5.

TABLE 4

| Lane | Substrate protein | Enzyme (amount added) |
| --- | --- | --- |
| 1 | Casein | *Rigidoporus laccase* (2.22 units) |
| 2 | Casein | *Rigidoporus laccase* (0.22 unit) |
| 3 | Casein | *Rigidoporus laccase* (0.02 unit) |
| 4 | Casein | No addition |
| 5 | BSA * | *Rigidoporus laccase* (2.22 units) |
| 6 | BSA | *Rigidoporus laccase* (0.22 unit) |
| 7 | BSA | *Rigidoporus laccase* (0.02 unit) |
| 8 | BSA | No addition |

*: Bovine serum albumin

TABLE 5

| Lane | Substrate protein | Enzyme (amount added) |
| --- | --- | --- |
| 1 | Casein | *Trachyderma tunodae bilirubin oxidase* (5.58 units) |
| 2 | Casein | *Trachyderma tunodae bilirubin oxidase* (0.558 unit) |
| 3 | Casein | *Trachyderma tunodae bilirubin oxidase* (0.056 unit) |
| 4 | Casein | No addition |
| 5 | BSA * | *Trachyderma tunodae bilirubin oxidase* (5.58 units) |
| 6 | BSA | *Trachyderma tunodae bilirubin oxidase* (0.558 unit) |
| 7 | BSA | *Trachyderma tunodae bilirubin oxidase* (0.056 unit) |
| 8 | BSA | No addition |

*: Bovine serum albumin

As shown in FIGS. 4 and 5, the cross-linked increase of molecular weight of each substrate protein was effected by both of the enzymes.

EXAMPLE 6

Production of Sausage Using *Pycnoporus coccineus* Laccase

*Pycnoporus coccineus* laccase was added in an amount of 1,000 units/g protein to 60% by weight of mince lean pork (3 mm), 20% by weight of mince pork fat (3 mm), 17% by weight of ice water, 1.5% by weight of kitchen salt, 0.5% by weight of seasonings and 0.5% by weight of spices, and the materials were mixed using a silent cutter, packed in a casing of about 2 cm in diameter, aged and dried at 55° C. for 60 minutes, smoked at 60° C. for 15 minutes and then cooked at 75° C. for 30 minutes. After cooling, gel strength evaluation and organoleptic test were carried out. A distinctively excellent sausage was prepared in comparison with a case in which laccase was not added.

EXAMPLE 7

Production of Fish Case (kamaboko) Using *Coriolus versicolor* Laccase

*Coriolus versicolor* laccase was added in an amount of 400 units/g protein to 100 parts by weight of fish meat (moisture, about 80%), 9 parts by weight of sucrose, 1 part by weight of sodium glutamate and 2% of sweet sake for seasoning (mirin), and the mixture was thoroughly kneaded, heaped up on a board and then cooked at 80 to 90° C. for 40 minutes. After cooling, elasticity of the product was measured using a rheometer. A kamaboko having distinctively excellent elasticity in comparison with a case in which laccase was not added was produced.

EXAMPLE 8

Production of Sausage Using *Myrothecium verrucaria* Bilirubin Oxidase in Stead of *Pycnoporus coccineus* Laccase A sausage was prepared in the same manner as described in Example 6. Gel strength evaluation and organoleptic test of the thus obtained product showed distinctively excellent results in comparison with a case in which bilirubin oxidase was not added.

According to the enzymatic protein cross-linking method of the present invention, certain proteins such as albumin, which cannot be cross-linked by the only microbial transglutaminase practically used so far, can also be cross-linked to effect increase of molecular weight. In addition, molecular weight-increased protein and gelled protein having new qualities can be produced.

While the invention has been described in detail and with reference to specific embodiments thereof, it will be apparent to one skilled in the art that various changes and modifications can be made therein without departing from the spirit and scope thereof.

This application is based on Japanese patent application No. Hei. 10-105729, filed on Mar. 31, 1998, and incorporated herein by reference.

What is claimed is:

1. A method for cross-linking a protein, which consists essentially of reacting a multi-copper oxidase with a protein, thereby effecting cross-linking of the protein.

2. The method according to claim 1, wherein the multi-copper oxidase is an at least one enzyme selected from the group consisting of laccase, bilirubin oxidase, ascorbic acid oxidase and ceruloplasmin.

3. The method according to claim 2, wherein the multi-copper oxidase is an at least one enzyme selected from the group consisting of laccase and bilirubin oxidase.

4. The method according to claim 1, wherein the multi-copper oxidase is used in an amount of from 0.5 to $1 \times 10^6$ units per 1 g of protein.

5. The method according to claim 4, wherein the multi-copper oxidase is used in an amount of from 5 to $1 \times 10^5$ units per 1 g of protein.

6. The method according to claim 1, wherein the reaction is carred out at the temperature of from 5 to 80° C.

7. The method according to claim 6, wherein the reaction is carried out at the temperature of from 20 to 60° C.

8. The method according to claim 1, wherein the reaction is carried out at pH of from 2 to 10.

9. The method according to claim 8, wherein the reaction is carried out at pH of from 4 to 8.

10. The method according to claim 1, wherein the reaction is carried out for the period of from 10 seconds to 48 hours.

11. The method according to claim 10, wherein the reaction is carred out for the period of from 10 minutes to 24 hours.

12. The method according to claim 3, wherein the multi-copper oxidase is laccase.

13. A method for cross-linking a protein, which comprises reacting a multi-copper oxidase selected from the group consisting of bilirubin oxidase, ascorbic acid oxidase and cerulopasmin with a protein, thereby effecting cross-linking of the protein.

14. The method according to claim 13, wherein said multi-copper oxidase is bilirubin oxidase.

15. The method according to claim 13, wherein the multi-copper oxidase is used in an amount of from 0.5 to $1 \times 10^6$ units per 1 g of protein.

16. The method according to claim 13, wherein the reaction is carried out at a temperature of from 5 to 80° C.

17. The method according to claim 13, wherein the reaction is carried out at a pH of from 2 to 10.

18. The method according to claim 13, wherein the reaction is carried out at for the period of from 10 seconds to 48 hours.

* * * * *